United States Patent [19]

Fishman

[11] Patent Number: 5,228,434
[45] Date of Patent: Jul. 20, 1993

[54] MIXTURE FOR ANESTHESIA
[75] Inventor: Royce S. Fishman, Iselin, N.J.
[73] Assignee: Praxair Technology, Inc., Danbury, Conn.
[21] Appl. No.: 806,380
[22] Filed: Dec. 13, 1991

Related U.S. Application Data

[62] Division of Ser. No. 730,703, Jul. 16, 1991, abandoned.
[51] Int. Cl.$^5$ .............................................. A61M 15/00
[52] U.S. Cl. ........................... 128/203.12; 128/200.24; 514/816
[58] Field of Search ....................... 128/203.12, 202.25, 128/200.24; 424/44, 600; 514/816

[56] References Cited

U.S. PATENT DOCUMENTS

| | | | |
|---|---|---|---|
| 3,527,205 | 9/1970 | Jones | 128/719 |
| 3,948,601 | 4/1976 | Fraser et al. | 422/23 |
| 4,233,842 | 11/1980 | Raemer et al. | 128/719 |
| 4,793,358 | 12/1988 | Kimura et al. | 128/654 |
| 5,088,499 | 2/1992 | Unger | 424/44 |

OTHER PUBLICATIONS

Rockoff, et al., Evaluation of Xenon as a Roentgenographic Contrast material, Am. Rev. of Respiratory Disease, vol. 86, pp. 434-438, Jan. 26, 1962.
Lachmann, et al., Safety and Efficacy of Xenon in Routine Use As An Inhalation Anesthetic, The Lancet, vol. 335, pp. 1413-1415, Jun. 16, 1990.
Broomsma, et al., Haemodynamic and Neurohumoral Effects of Xenon Anesthesia, Anesthesia, vol.45, pp. 273-278, 1990.

Primary Examiner—Edgar S. Burr
Assistant Examiner—Aaron J. Lewis
Attorney, Agent, or Firm—Stanley Ktorides

[57] ABSTRACT

A method for anesthetizing a patient comprising providing to the patient for breathing stable xenon, oxygen and helium and a gas mixture suitable therefor.

6 Claims, 1 Drawing Sheet

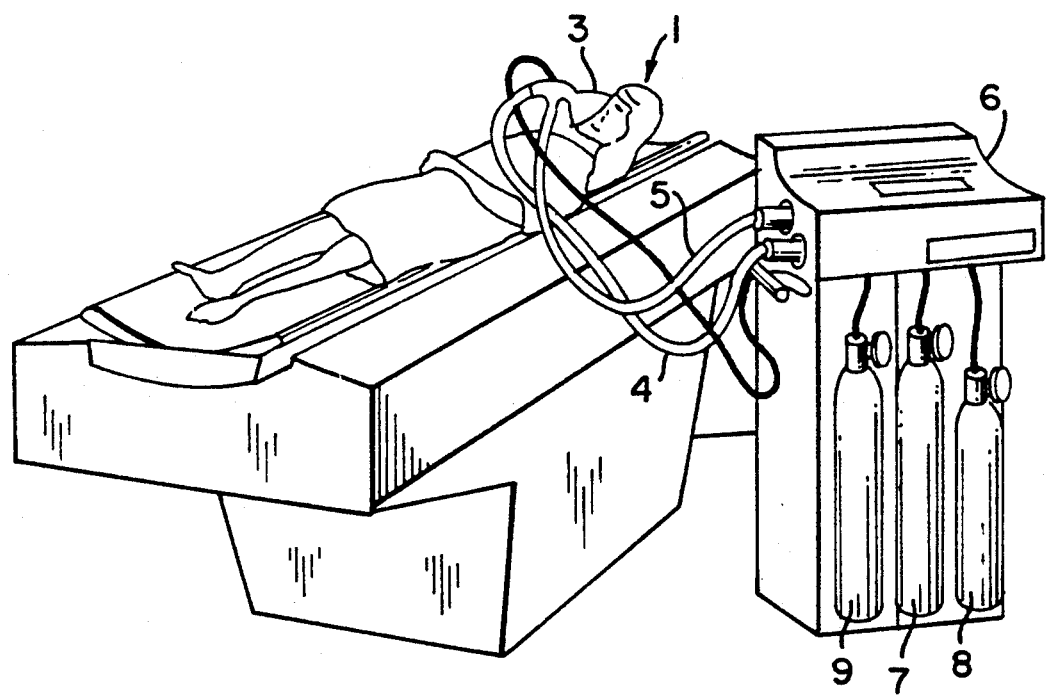

MIXTURE FOR ANESTHESIA

This application is a division of prior U.S. application Ser. No. 730,703, filing date Jul. 16, 1991, now U.S. Pat. No. 5,099,834 issued Mar. 31, 1992.

TECHNICAL FIELD

This invention relates to anesthesia wherein a gas is breathed by the patient to anesthetize the patient.

BACKGROUND ART

There are several known ways to anesthetize a patient. One important method for anesthetizing a patient in preparation for, for example, dental, obstetric, gynecological, plastic, orthopedic or other surgery, is to administer a gas to the patient by inhalation. The anesthetic gas passes into the patient's lungs and then into the patient's bloodstream by which it is delivered to the nervous system to perform the anesthetic function.

The most widely used gas employed as an anesthetic is nitrous oxide. This gas is an effective anesthetic and is relatively inexpensive. However, recently, questions have arisen regarding the safety of nitrous oxide. Specifically, it has been reported that nitrous oxide is chemically active and may undergo biotransformation to metabolites that could be toxic, is metabilicaly actie, is a fetal toxin, can cause spontaneous abortions (miscarriages), is a carcinogen and has cardio suppressive properties. It is commonly used with an induction or co-general anesthetic medication for other than dental surgery. This can prolong the period of the patient to recover consciousness following surgery. Nitrous oxide is also a strong oxidizer and can vigorously support combustion if present in sufficient quantity by accident or lack of unawareness in an operatorium, representing a hazard to both the patient and medical staff. Accordingly, it is desirable to be able to carry out anesthesia by patient inhalation without employing nitrous oxide and without significantly increasing the cost of the anesthetic procedure.

Nitrous oxide can inactivate certain enzymes by oxidizing the cobalt in vitamin B12. This can lead to a decrease in serum methionine, which reduces the conversion of uridine to thymidine, one of the four nucleotides of deoxyribonucleic acid (DNA). The overall effect is a decrease in DNA production resulting in the inhibition of cell division. Tissue with a high rate of cell turnover would be most susceptible, possibly explaining the reproductive and carcinogenic problems nitrous oxide can cause.

The fetal toxicity of nitrous oxide raises particular problems. Women may not be aware that they are pregnant in the early stages of pregnancy. The use of nitrous oxide at this stage can have unfortunate consequences including spontaneous abortions, which have been reported. Since all women of childbearing age would be at risk of having nitrous oxide administered in the early stages of a pregnancy, all uses of nitrous oxide on women who are menstruating and/or who are premenopause, would require testing prior to use to establish the absence of a pregnancy. This approach is not practiced and the procedure is costly and time consuming and can never be absolutely accurate.

In addition to the concern for patient exposure to nitrous oxide, it has also been noted that medical professionals who work in dental and surgical operatoriums where concentrations of waste nitrous oxide present in the room environment exceed recommendations by federal agencies such as NIOSH, have a higher incidence of spontaneous abortions/miscarriages and fetal malformations than control groups. It has been found that many operatoriums exceed the recommendations.

Accordingly, it is an object of this invention to provide a method for anesthetizing a patient by the patient's inhalation of a gas which does not include nitrous oxide.

SUMMARY OF THE INVENTION

The above and other objects, which will become apparent to one skilled in the art upon a reading of this disclosure, are attained by the present invention, one aspect of which is:

A method of anesthetizing a patient comprising providing to the patient for inhalation by the patient a gas mixture comprising from 60 to 78.5 mole percent stable xenon, from 19.5 to 38 mole percent oxygen and from 2.5 to 20.5 mole percent helium in a sufficient amount and for a sufficient time period to anesthetize the patient.

Another aspect of this invention is:

A method for anesthetizing a patient comprising providing to the patient for inhalation by the patient a first gas mixture comprising from 19.5 to 90 mole percent oxygen and from 10 to 80.5 mole percent the helium and thereafter providing to the patient for inhalation by the patient a second gas mixture comprising from 19.5 to 40 mole percent oxygen and from 60 to 80.5 mole percent stable xenon in a sufficient amount and for a sufficient time period to anesthetize the patient.

A further aspect of this invention is:

A mixture comprising from 60 to 78.5 mole percent stable xenon, from 19.5 to 38 mole percent oxygen and from 2.5 to 20.5 mole percent helium.

As used herein the term "anesthetize" means to induce a loss of sensation and usually of consciousness without loss of vital functions artificially produced by the administration of one or more agents that block the passage of pain impulses along nerve pathways of the brain. The ability of an agent to cause anesthesia is based on the MAC or minimum leveler concentration required for the absence of a response to a surgical incision in 50 percent of patients. The MAC value for xenon is 70–71 percent.

As used herein the term "stable xenon" means the non-radioactive form of xenon having an atomic weight of about 131.29 and an atomic number of 54.

BRIEF DESCRIPTION OF THE DRAWING

The sole Figure is a representation of a human subject being given a gas mixture in the practice of the invention.

DETAILED DESCRIPTION

The invention is an improved method of anesthetizing a patient. The invention comprises in general the provision of stable xenon along with oxygen and helium to a patient, human or veterinary, in order to carry out the anesthetizing. The oxygen serves to provide life support for the patient. The stable xenon diffuses into the blood stream and acts as the anesthetizing agent. Because xenon is a relatively dense gas, at high concentrations it can potentially require greater effort by the patient for respiration if the patient is not on a respirator or ventilator, although not at a level placing the patient in distress or danger. Because of its density and the fact that a patient undergoing surgery may be in a supine or upright position for an extended period of time, a gas mixture with a high percentage of xenon may focus its flow to the lowest area of the lungs due to gravity, resulting in an uneven distribution of the xenon throughout the lungs regardless of whether the patient is on a respirator or ventilator. Because of its low density compared to xenon, helium reduces the density of the total anesthetic gas mixture delivered to the patient. This reduces flow resistance, reduces respiratory work and/or supports the more even distribution of the anesthetic xenon gas within the lungs during a surgical procedure.

In one embodiment of the invention, the three gases are provided to the patient simultaneously as a gas mixture. The gas mixture comprises from 60 to 78.5 mole percent, preferably from 65 to 78.5 mole percent stable xenon, from 19.5 to 38 mole percent, preferably from 20 to 24 mole percent, oxygen, and from 2.5 to 20.5 mole percent, preferably from 7.5 to 15 mole percent helium. The gas mixture may be administered to the patient directly from a cylinder or tank wherein it has been premixed, or it may be made up at the anesthetizing site from components taken from a plurality of cylinders or tanks. While providing improved safety over nitrous oxide, this is not a cost effective approach. The gas mixture may also be delivered to the patient by a rebreathing system which uses a plurality of cylinders or tanks containing xenon, helium and oxygen to maintain a constant percentage of each gas in the rebreathing chamber for administration to the patient as required for a specific procedure, with the patient's exhalation passing through bacterial and carbon dioxide filters prior to re-entering the rebreathing chamber. This approach provides improved safety and is cost effective. The gas mixture is provided to the patient in a sufficient amount for a sufficient time period to anesthetize the patient. The amount and time will vary and will depend on factors such as the particulars of the patient and of the surgery. The gas mixture will be provided to the patient throughout the surgery for as long as an anesthetized state is required.

In another embodiment of the invention the patient is first provided for inhalation a gas mixture comprising from 19.5 to 90, preferably from 20 to 40, mole percent oxygen and from 10 to 80.5, preferably from 60 to 80, mole percent helium; thereafter the patient is provided for inhalation a gas mixture comprising from 19.5 to 40, preferably from 20 to 40, mole percent oxygen and from 60 to 80.5, preferably from 60 to 80, mole percent stable xenon. The mixture comprising oxygen and helium is employed to substantially purge the patient's lungs of gases other than helium and oxygen and thus make the patient particularly amenable to the anesthetizing effects of the mixture of stable xenon and oxygen which is thereafter administered. The mixture comprising stable xenon and oxygen is provided to the patient in a sufficient amount and for a sufficient time period to anesthetize the patient. The amount and time will vary and will depend on factors such as the particulars of the patient and of the surgery. The mixture comprising stable xenon and oxygen will be provided to the patient throughout the surgery for as long as an anesthetized state is required.

If desired, the gas mixture comprising 19.5 to 90, preferably from 20 to 40, mole percent oxygen and from 10 to 80.5, preferably from 60 to 80, mole percent helium may be provided to the patient for purging purposes prior to the administration of the gas mixture comprising xenon, oxygen and helium described above.

Xenon is a monatomic gas which lacks a permanent dipole moment and is therefore devoid, in biological systems, of the complexities of chemical reactivity inherent in molecules which can combine through covalent, ionic or hydrogen bonds with the chemical constituents of biological systems. It weakly binds to hemoglobin in the blood based on Van der Waals forces. It is unchanged by the body and is exhaled. It is non-volatile, non-combustible and non-explosive. It has minimal effect on blood chemistry, is not toxic in general, is not fetal toxic, is not carcinogenic, is not cardiosuppressive and has slightly greater anesthetic properties then nitrous oxide. Depending on the patient and surgery, it can require no to as little as one fifth as much of an induction pharmaceutical such as fentynal as does nitrous oxide. This, combined with the lack of bioreactivity and rapid elimination of xenon from the body after administration is ended, makes xenon a rapidly reversible anesthetic. The result is more rapid recovery from the anesthesia.

After the surgery the patient may be returned to consciousness by the normal effects of removing the xenon from his system by breathing air, or the process may be accelerated by the administration of pure oxygen for, for example, 5 to 10 minutes after the administration of the xenon comprising mixture has been terminated.

The Figure illustrates the use of one embodiment of the invention wherein the anesthetic is administered to the patient as a gas mixture which is made up at the site of the anesthetic procedure. Referring to the Figure there is illustrated a human patient 1 on an operating room table. The gas mixture is administered to patient 1 through face mask 3 into which gas flows through line 4 and out from which exhalant flows through line 5. The gas mixture is made u by mechanical gas mixing device 6 which takes gas components from one or more cylinders. In the Figure there are illustrated three such cylinders 7, 8 and 9. For example, cylinder 7 may contain xenon, cylinder 8 may contain oxygen and cylinder 9 may contain helium. The gases are blended by gas mixer 6 to make up the gas mixture for use in the invention and the gas mixture is administered to the patient. After the gas mixture has been so administered and the patient has been anesthetized, the patient undergoes a medical procedure such as dental, obstetric, gynecological, plastic, orthopedic or other surgery with the continued administration of the anesthetic.

In the practice of another embodiment of the invention, two cylinders containing oxygen and xenon respectively could provide gas to a gas mixer to make up a mixture comprising oxygen and xenon for administration to the patient after the patient's lungs have been purged by the administration of a gas mixture comprising oxygen and helium.

The invention provides advantages over existing practices. The use of xenon avoids the necessity of using potentially fetal toxic, carcinogenic and cardiosuppressive nitrous oxide in the anesthetic procedure. This is particularly important for the anesthetizing of women of childbearing age since the danger of harm to a fetus from nitrous oxide is eliminated. Moreover, with the use of the invention, no or less premedication or induction, or co-general anesthetic pharmaceutical need be used than is required with nitrous oxide thus reducing the recovery time needed after the surgery. In addition the presence of helium effectively reduces the density of the gas mixture and thereby reduces the effort required for respiration and improves the distribution of the anesthetic gas mixture in the lungs.

The following example will serve to further illustrate the invention. It is presented for illustrative purposes and is not intended to be limiting.

A female patient of childbearing age undergoes surgery, e.g., plastic surgery. No premedication need be given. Methyl-atrophine bromide (0.002 mg/kg intraveneously) and 500 ml Ringer's lactate solution may precede induction of anesthesia with thiopentone (2.5-5 mg/kg) and 0.1 mg fentanyl. Tracheal intubation may be facilitated by 0.1 mg/kg pancuronium. The patient is then given 100 percent oxygen for 5-8 minutes to denitrogenate or remove the nitrogen from the lungs. The patient is then administered a mixture comprising 70 percent xenon, 10 percent helium, and 20 percent oxygen for the duration of surgery of about one hour. The xenon mixture is administered to the patient by a rebreathing system slaved to a respirator/ventilator to support adequate and timely respiration by the patient, which continuously adjusts the gas mixture to that desired by the clinician from a plurality of cylinders or tanks containing xenon, helium and oxygen, making its use cost effective. Exhaled gases are scrubbed for bacteria by a 0.22 micron filter and for carbon dioxide by an absorbent filter before reentering the rebreathing chamber of the delivery device. Following completion of surgery, the flow of the gas mixture containing xenon is stopped and the mask is removed from the patient. The patient regains consciousness in as little as 2 minutes. The patient may be administered 100 percent oxygen for, for example, 3-5 minutes to accelerate the purging of xenon from the body thereby accelerating recovery of consciousness.

The anesthetic mixture of this invention may also be used in dental surgery such as tooth extraction, root canal, or in other minor surgical procedures such as inguinal herioplasties or laser laproscopy, which may be performed using only the gas mixture as the general anesthetic as a replacement for nitrous oxide, with other potions of the surgical procedure remaining the same.

The patient may for example be administered the gas mixture directly from a single pre-mixed cylinder or tank, or from a plurality of cylinders or tanks through a rebreathing delivery device as described above. A respirator/ventilator may not be required, but is preferred from the standpoint of safety. Following the end of the procedure, purging the xenon from the patient's body maybe accelerated by the administration of 100 percent oxygen for 3-5 minutes, accelerating recovery of consciousness. The performance of procedures with only the anesthetic mixture of this invention and without an induction or co-general anesthetic pharmaceutical, combined with the rapid purging from the body with, for example, 100 percent oxygen, would allow the performance of outpatient procedures enabling patients to travel by themselves to their homes within a short time after completion of a procedure after and/or if they have recovered sufficiently and if the nature of the surgery does not require a lack of exertion of strain.

Those skilled in the art will recognize that although the invention has been described in detail with reference to certain specific embodiments, there are other embodiments of the invention within the spirit and the scope of the claims.

I claim:

1. A mixture consisting of from 60 to 78.5 mole percent stable xenon, from 19.5 to 38 mole percent oxygen and from 2.5 to 20.5 mole percent helium.

2. The mixture of claim 1 wherein e mixture is a gas mixture which is particularly useful as an anesthetic by patient inhalation.

3. The mixture of claim 1 contained in a cylinder.

4. The mixture of claim 1 wherein the xenon is present in a concentration within the range of rom 65 to 78.5 mole percent.

5. The mixture of claim 1 wherein the oxygen is present in a concentration within the range of from 20 to 24 mole percent.

6. The mixture of claim 1 wherein the helium is present in a concentration within the range of from 7.5 to 15 mole percent.

* * * * *

UNITED STATES PATENT AND TRADEMARK OFFICE
CERTIFICATE OF CORRECTION

PATENT NO. : 5,228,434
DATED : July 20, 1993
INVENTOR(S) : R. S. Fishman

It is certified that error appears in the above-identified patent and that said Letters Patent is hereby corrected as shown below:

On the Title page, item [62] after "1991", delete "abandoned" and insert therefor -- now U.S. Patent No. 5,099,834 --.

In column 1, line 27 delete "toxid, is metabilicaly actie" and insert therefor -- toxic, is metabolically active --.

In column 4, line 38 after "made" delete "u" and insert therefor -- up --.

In column 6, line 8 delete "maybe" and insert therefor -- may be --.

In column 6, line 19 delete "of" second occurrence and insert therefor -- or --.

In claim 2, line 1 after "wherein" delete "e" and insert therefor -- the --.

In claim 4, line 2 delete "rom" and insert therefor -- from --.

Signed and Sealed this

Twenty-second Day of February, 1994

Attest:

BRUCE LEHMAN

Attesting Officer    Commissioner of Patents and Trademarks